United States Patent
Ryu et al.

(10) Patent No.: US 9,675,731 B2
(45) Date of Patent: Jun. 13, 2017

(54) BONE GRAFT COMPOSITION AND PREPARATION METHOD THEREOF

(71) Applicant: Bioalpha Corporation, Seoul (KR)

(72) Inventors: Mi Young Ryu, Gyeonggi-do (KR); Nam Yul Cho, Gyeonggi-do (KR); Jun Hyuk Seo, Gyeonggi-do (KR); Hyun Seung Ryu, Gyeonggi-do (KR); So Myoung Lee, Gyeonggi-do (KR)

(73) Assignee: Bioalpha Corporation, Seoul (KR)

( * ) Notice: Subject to any disclaimer, the term of this patent is extended or adjusted under 35 U.S.C. 154(b) by 0 days.

(21) Appl. No.: 14/780,814

(22) PCT Filed: Mar. 28, 2014

(86) PCT No.: PCT/KR2014/002659
§ 371 (c)(1),
(2) Date: Sep. 28, 2015

(87) PCT Pub. No.: WO2014/157985
PCT Pub. Date: Oct. 2, 2014

(65) Prior Publication Data
US 2016/0051725 A1 Feb. 25, 2016

(30) Foreign Application Priority Data
Mar. 28, 2013 (KR) .................. 10-2013-0033859

(51) Int. Cl.
*A61F 2/28* (2006.01)
*A61L 27/12* (2006.01)
(Continued)

(52) U.S. Cl.
CPC ............ *A61L 27/12* (2013.01); *A61F 2/28* (2013.01); *A61L 27/02* (2013.01); *A61L 27/14* (2013.01);
(Continued)

(58) Field of Classification Search
CPC .......... A61L 27/02; A61L 27/52; A61L 27/14; A61F 2/28
See application file for complete search history.

(56) References Cited

U.S. PATENT DOCUMENTS

| | | |
|---|---|---|
| 5,717,006 A | 2/1998 | Daculsi et al. |
| 6,599,516 B1 | 7/2003 | Knaack |

(Continued)

FOREIGN PATENT DOCUMENTS

| | | |
|---|---|---|
| KR | 10-2005-0012230 | 1/2005 |
| KR | 10-2006-0133961 | 12/2006 |

(Continued)

OTHER PUBLICATIONS

Kretlow et al, "Injectable Biomaterials for Regenerating Complex Craniofacial Tissues", Adv Mater. Apr. 20, 2009; 21(32-33); 3368-3393.*

*Primary Examiner* — Carlos Azpuru
(74) *Attorney, Agent, or Firm* — Cesari and McKenna LLP (57) ABSTRACT

The present invention relates to a bone graft composition and a preparation method thereof, and more particularly to a bone graft composition having excellent physical properties, which comprises a hydrogel comprising a combination of specific amounts of poloxamer and HPMC, and calcium phosphate compound particles, and a preparation method thereof.

20 Claims, 9 Drawing Sheets

(51) Int. Cl.
*A61L 27/14* (2006.01)
*A61L 27/02* (2006.01)
*A61L 27/52* (2006.01)
*A61L 27/46* (2006.01)
*A61L 27/54* (2006.01)
*A61L 27/18* (2006.01)
*A61L 27/20* (2006.01)

(52) U.S. Cl.
CPC ............... *A61L 27/18* (2013.01); *A61L 27/20* (2013.01); *A61L 27/46* (2013.01); *A61L 27/52* (2013.01); *A61L 27/54* (2013.01); *A61L 2300/414* (2013.01); *A61L 2430/02* (2013.01)

(56) References Cited

U.S. PATENT DOCUMENTS

| | | |
|---|---|---|
| 7,771,755 B2 | 8/2010 | Li et al. |
| 8,574,611 B2 | 11/2013 | Seibl et al. |
| 8,603,184 B2 | 12/2013 | Rizzoli et al. |

FOREIGN PATENT DOCUMENTS

| | | | |
|---|---|---|---|
| KR | 10-0859889 | 9/2008 | |
| KR | 10-2099-0112967 | 10/2009 | |
| KR | 10-2010-0061649 | 6/2010 | |
| KR | 10-2012-0116215 | * 10/2012 | ............. A61K 16/47 |
| WO | WO-2011/137231 A1 | 11/2011 | |
| WO | WO-2012/117260 A1 | 9/2012 | |

* cited by examiner

BONE GRAFT COMPOSITION AND PREPARATION METHOD THEREOF

CROSS-REFERENCE TO RELATED APPLICATIONS

This application is the National Stage of International Application No. PCT/KR2014/002659, filed on Mar. 28, 2014, which claims the benefit of Korean Application No. 10-2013-0033859, filed on Mar. 28, 2013. The contents of both applications are hereby incorporated by reference in their entirety.

TECHNICAL FIELD

The present invention relates to a bone graft composition and a preparation method thereof, and more particularly to a bone graft composition having excellent physical properties, which comprises a hydrogel comprising a combination of specific amounts of poloxamer (PEO-PPO-PEO block co-polymer) and HPMC (Hydroxy-Propyl Methyl-Cellulose), and calcium phosphate compound particles, and a preparation method thereof.

BACKGROUND ART

Bone graft biomaterials developed in the initial stage have a characteristic in that they are inert in vivo, but the use thereof was significantly limited due to infection and inflammatory reaction, which occur in the surrounding tissue after implantation. Since then, with the rapid development of biomaterial technologies based on ceramic and polymer materials, materials that are biocompatible rather than bio-inert were designed and developed, leading to the development of bioactive scaffolds for bone tissue regeneration, which vary depending on the site and purpose of use. It is required that such bioactive scaffolds for bone tissue regeneration should have different physical properties depending on the location of graft placement, should not be toxic to the surrounding tissue, and should have relatively high mechanical properties compared to other artificial organs. Such bioactive scaffolds for bone tissue regeneration have been marketed and developed as various biomaterials depending on the properties of the raw materials and the intended use thereof.

All materials that are to be grafted into the human body, particularly polymer materials for bone tissue regeneration, should have good processability and moldability or have good in-situ polymerization properties so as to be suited to wounds. These materials are required to provide a suitable environment for the adhesion, growth and differentiation of cells, and degradation products thereof are also required to be bio-compatible. Particularly, if the compressive strength and yield strength of a bone graft material are too low, it will be difficult to maintain the abilities of the bone graft material to fix its location and keep its external shape in the closure or implant placement stage after injection or dense filling of the bone graft material. In addition, if the adhesiveness of a bone graft material is too high, it will easily stick to a surgical tool during surgery, and thus will be difficult to easily fill in bone defects, resulting in a decrease in workability.

Accordingly, there is a need for the development of a bone graft composition that has biocompatibility and physical properties suitable for grafting in bone defects and that has the property of maintaining the formulation during a specific period after implantation.

DISCLOSURE OF INVENTION

Technical Problem

Under this background, the present inventors have prepared a bone graft composition using a hydrogel comprising a combination of specific amounts of poloxamer and HPMC, and calcium phosphate compound particles, and have found that the composition have physical properties suitable for use as a bone graft material, thereby completing the present invention.

Solution to Problem

It is an object of the present invention to provide a bone graft composition having excellent physical properties.

Another object of the present invention is to provide a method for preparing a bone graft composition having excellent physical properties.

Advantageous Effects of Invention

According to the present invention, a bone graft composition that is better in terms of compressive strength, yield strength and adhesiveness compared to a hydrogel of poloxamer alone or a hydrogel comprising poloxamer and HPMC in amounts out of the ranges specified in the present invention can be provided by the use of a hydrogel comprising a combination of specific amounts of poloxamer and HPMC.

BRIEF DESCRIPTION OF DRAWINGS

FIGS. 4a-4f shows the change in the physical properties of a bone graft composition as a function of the content of β-TCP powder. Specifically.

FIG. 7a shows the results for the bone graft composition of Comparative Example 1, and FIG. 7b shows the results for the bone graft composition of Example 1.

BEST MODE FOR CARRYING OUT THE INVENTION

To achieve the above objects, the present invention provides a bone graft composition comprising:

A) 30-55 wt % of calcium phosphate compound particles; and

B) 45-70 wt % of a biodegradable hydrogel containing, based on 100 parts by weight of the hydrogel, 25-35 parts by weight of poloxamer and 0.5-2 parts by weight of hydroxypropyl methylcellulose (HPMC).

The present invention is characterized in that a bone graft composition having excellent physical properties can be provided by mixing calcium phosphate compound particles with a hydrogel comprising a combination of specific amounts of poloxamer and HPMC. Specifically, a mixture of hydrogel and calcium phosphate compound particles can be injected and can be densely filled in irregular bone defects.

In other words, it is possible to provide a bone graft composition that can be biodegraded with the passage of time after bone grafting, because it comprises the biodegradable polymers poloxamer and HPMC. Also, the bone graft composition has high compressive strength and yield strength, and thus has an excellent ability to keep its volume in the body temperature range after bone grafting, because it comprises a hydrogel comprising a combination of specific amounts of poloxamer and HPMC. In addition, the bone graft composition comprises a hydrogel and calcium phosphate compound particles at a suitable mixing ratio, and thus may have a formulation such as a putty type material resulting from the agglomeration of the hydrogel and the calcium phosphate compound particles. At the same time, the bone graft material has low adhesiveness, so that it does not stick to a surgical tool during surgery, and thus it does not stick to a surgical tool when it is filled in bone defects, suggesting that it has an advantage of excellent workability.

As used herein, the term "bone graft composition" refers to a composition for use as bone defect replacement that is grafted in bone defects to fill the bone defects. Specifically, the term "bone graft composition" as used herein means an alloplastic synthetic bone graft material composition based on a calcium phosphate compound.

The bone graft composition of the present invention is mainly composed of calcium phosphate compound particles and a hydrogel.

As the first component of the bone graft composition of the present invention, calcium phosphate compound particles are similar to natural bone and functions to induce osteoconduction and bone growth.

As used herein, the term "calcium phosphate compound" refers to a compound comprising phosphoric acid and calcium.

In the present invention, the calcium phosphate compound may be tricalcium phosphate (TCP), monocalcium phosphate, tetracalcium phosphate, dicalcium phosphate, hydroxyapatite, or a combination of two or more thereof, but is not limited thereto.

Preferably, the tricalcium phosphate may be β-tricalcium phosphate (β-TCP; $Ca_3(PO_4)_2$).

In an example of the present invention, β-TCP was used because of its excellent osteoconductivity.

In the present invention, the β-TCP may preferably be in the form of microspheres.

In the present invention, the β-TCP may be obtained by spray-drying β-TCP powder, sintering the dried powder at a temperature of 1050-1250° C., and classifying the sintered powder in the range of 45 to 75 μm. More specifically, the β-TCP can be obtained by spray-drying β-TCP powder to form a spherical shape and sintering the spherical β-TCP powder at a temperature of 1050-1250° C. to increase the porosity of the powder. In order to obtain a more uniform bone graft composition, the sintered β-TCP powder may be classified in the range of 45 to 75 μm. The sintering may be performed for 1-3 hours. Most preferably, the sintering may be performed for 2 hours.

The resulting β-TCP particles obtained as described above may be microspherical particles having a diameter of 45-75 μm. Moreover, the resulting β-TCP particles may have a porosity of 60% or higher as a result of performing the spray-drying and sintering processes as described above.

Thus, as one preferred aspect of the invention, the present invention provides a bone graft composition comprising:

A) 30-55 wt % of calcium phosphate compound particles in the form of microsphere; and B) 45-70 wt % of a biodegradable hydrogel containing, based on 100 parts by weight of the hydrogel, 25-35 parts by weight of poloxamer and 0.5-2 parts by weight of hydroxypropyl methylcellulose (HPMC).

As the second component of the bone graft composition of the present invention, the hydrogel is a gel formed by dispersing a polymer having a sol-gel transition property in water and functions to agglomerate the calcium phosphate compound particles to form a formulation suitable for bone grafting.

The present invention is characterized in that poloxamer and hydroxypropyl methylcellulose (HPMC) are used as biodegradable polymers, which have a sol-gel transition temperature lower than the body temperature and can maintain the gel state in the body temperature range, in order to provide a bone graft composition that is biocompatible and have an excellent ability to maintain its formulation after implantation.

As used herein, the term "poloxamer" refers to a triblock copolymer (PEO-PPO-PEO) having two polyethylene glycol (PEG) chains bonded to a central chain of polypropylene glycol (PPG). Generally, the ratio of PEG/PPG in poloxamer may vary in the range from 1:9 to 8:2. The molecular weight of poloxamer may be in a wide range from 1,100 to 14,000 g/mole. Poloxamer is a temperature-sensitive polymer. In the present invention, poloxamer functions to impart injectability and moldability to the bone graft composition and to enable the bone graft material to be degraded rapidly after filling in bone defects so as to allow only the calcium phosphate-based bone graft material component to remain. In order to maintain the ease of injection and moldability in the room temperature range and formulation stability during storage and transport at room temperature, high-molecular-weight poloxamer having a relatively low sol-gel transition temperature and high viscosity is preferably used. More preferably, poloxamer that has a sol-gel transition temperature of 4~35° C. so as to be able to maintain the gel state at about 37° C. (body temperature) may be used in the present invention. Most preferably, poloxamer 407 having an excellent ability to maintain the gel state at about 37° C. (body temperature) may be used in the present invention.

As used herein, the term "hydroxypropyl methylcellulose (HPMC)" refers to a semi-synthetic, inert, viscoelastic polymer, also called hypromellose. In the present invention, HPMC functions to improve the elasticity of the hydrogel. Particularly, as the viscoelasticity of the hydrogel increases, the ability to fix the location of the bone graft material when filling bone defects becomes better so that the leakage of the bone graft material to the outside can advantageously be minimized.

Accordingly, the viscosity of HPMC in the present invention may preferably be 1,000-100,000 cps, and most preferably 100,000 cps. HPMC in the present invention is added in a trace amount in order to induce high viscosity and high elasticity, and as the viscosity thereof increases, the ability to fix the location of the bone graft material and the density of filling of the bone graft material can be increased, and the adhesion of the bone graft material to a surgical tool and gloves can be minimized. Thus, it is most preferable to use HPMC having a viscosity of 100,000 cps, which shows the highest viscosity when being added in a trace amount.

In the present invention, the bone graft composition may further comprise bone morphogenetic protein (BMP).

In the present invention, the bone morphogenetic protein may be BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, or a combination of two or more thereof, but is not limited thereto.

In the present invention, the putty-type bone graft composition may be placed in an injection tool such as a syringe or a tube and injected into a desired position. After injection, the bone graft composition may be crammed by a surgical tool so that it is densely filled in bone defects due to the viscoelastic property of the bone graft composition.

According to the present invention, the hydrogel comprising a combination of specific amounts of poloxamer and HPMC as described above is used, thereby providing a bone graft composition that is better in terms of compressive strength, yield strength and adhesiveness compared to a hydrogel comprising poloxamer alone or a hydrogel comprising poloxamer and HPMC in amounts out of the above-described ranges.

Particularly, the bone graft composition of the present invention may have a yield strength ranging from 1500 to 4000 g/cm$^2$. When the bone graft composition of the present invention has a yield strength within the above-described range, it will exhibit excellent viscoelasticity, and thus can be easily filled in bone defects during grafting, suggesting that it shows physical properties suitable for use as a bone graft material.

As used herein, the term "compressive strength" is used interchangeably with "strength" and means the strength at which the external shape of the bone graft composition is changed by an external force. The term "yield strength" is a physical property value related to the elasticity of the bone graft composition and means the maximum strength to which the bone graft composition is not deformed by an external force. Thus, as the compressive strength and yield strength of the bone graft composition increase, it is possible to maintain the abilities of the bone graft composition to fix its location and maintain its external shape in the implant placement stage after injection or dense filling of the bone graft composition.

As used herein, the term "adhesiveness" means the property of adhering to stainless steel. It is a force acting in a direction opposite to compressive strength, and (−) means only direction. The higher absolute value of the adhesiveness means that a greater force is required to detach the bone graft composition formulation that stuck to stainless steel. In addition, the absolute value of the adhesiveness may mean the degree of adhesion of the bone graft composition formulation not only to a surgical tool made of stainless steel, but also to gloves made of resin.

Compressive strength, yield strength and adhesiveness, which are physical strengths that are measured in the present invention, may be measured using a conventional rheometer.

The bone graft composition of the present invention as described above comprises a hydrogel filled between calcium phosphate compound particles closed to each other. After implantation of the bone graft composition into bone defects, the hydrogel is degraded and released, the calcium phosphate compound particles are maintained in the close state, and bone grows into the space between the calcium phosphate compound particles after release of the hydrogel.

The present invention also provides the use of the bone graft composition for bone grafting.

The present invention also provides a method for preparing the bone graft composition, the method comprising the steps of:

1) preparing a biodegradable hydrogel containing, based on 100 parts by weight of the hydrogel, 25-35 parts by weight of poloxamer and 0.5-2 parts by weight of hydroxypropyl methylcellulose (HPMC); and 2) mixing 30-55 wt % of calcium phosphate compound particles with 45-70 wt % of the biodegradable hydrogel.

Step 1) is a step of preparing a biodegradable hydrogel containing, based on 100 parts by weight of the hydrogel, 25-35 parts by weight of poloxamer and 0.5-2 parts by weight of hydroxypropyl methylcellulose (HPMC). In this step, predetermined amounts of poloxamer and HPMC are dispersed in water to prepare a biodegradable hydrogel.

Preferably, in step 1), HPMC is first dispersed in water to form a HPMC gel, and when the HPMC is completely dispersed, poloxamer is added to and dispersed in the HPMC gel, thereby preparing a hydrogel comprising poloxamer and HPMC.

"Poloxamer 407 is a triblock copolymer consisting of a central hydrophobic block of polypropylene glycol flanked by two hydrophilic blocks of polyethylene glycol (PEG). The approximate lengths of the two PEG blocks is 101 repeat units while the approximate length of the propylene glycol block is 56 repeat units."

Because HPMC does not dissolve in a gel state due to its high viscoelasticity, the hydrogel is preferably prepared by the above-described method in which HPMC is first added to water to make a gel, and then poloxamer is added thereto. If HPMC is added to poloxamer gel, HPMC will agglomerate and will not disperse in the gel. In addition, even in the case in which HPMC is first gelled, a gel phase can be easily formed only when HPMC is dissolved while water is added thereto in small amounts.

Thus, step 1) may preferably comprise the steps of:

a) adding HPMC to an amount of water corresponding to ¼ to ½ of the total amount of water used, and then stirring the HPMC at a speed of 300-500 rpm in a vacuum state to form a hard HPMC gel;

b) adding two to four equally divided parts of the remaining amount of water stepwise to dilute the gel; and c) adding poloxamer to the HPMC gel at a time, followed by stirring at a speed of 300-500 rpm in a vacuum state.

The kinds of poloxamer and HPMC are as described with respect to the bone graft composition.

Step 2) is a step of mixing 30-55 wt % of calcium phosphate compound particles with 45-70 wt % of the biodegradable hydrogel. In this step, a predetermined amount of the hydrogel gel prepared in step 1) is mixed with a predetermined amount of calcium phosphate compound particles to obtain a bone graft composition.

The characteristics and preparation method of the calcium phosphate compound particles are as described with respect to the bone graft composition.

In a preferred embodiment of the present invention, the calcium phosphate compound particles may be prepared in the following manner.

Pure β-TCP powder is spray-dried to prepare spherical powder. Then, the spherical β-TCP powder is sintered at a temperature of 1050° C. Next, the sintered particles are classified in the range of 45-75 μm.

In step 2), bone morphogenetic protein (BMP) may further be added and mixed.

The kind of bone morphogenetic protein (BMP) is as described with respect to the bone graft composition.

In a preferred embodiment of the present invention, the bone graft composition may be prepared in the following manner.

First, 1 g of HPMC and 10 ml of purified water are placed in a high-speed vacuum mixer and uniformly mixed with each other at a speed of 400 rpm. Then, 10 ml of purified water is added to the semi-transparent jelly-like HPMC gel and mixed at the same speed. Then, 14 ml of purified water is added to the HPMC gel, followed by uniform mixing. Next, 15 g of poloxamer 407 is added to HPMC gel, followed by mixing at a speed of 400 rpm (30 wt % of poloxamer and 2 wt % of HPMC hydrogel). 50 g of β-TCP microspheres are added to the resulting gel, and followed by uniform mixing at a speed of 200 rpm or lower.

In the present invention, the putty-type bone graft composition prepared as described above may be placed in a syringe and injected into a desired position.

The present invention also provides a composition for use in bone implantation comprising:

A) 30-55 wt % of calcium phosphate compound particles; and

B) 45-70 wt % of a biodegradable hydrogel containing, based on 100 parts by weight of the hydrogel, 25-35 parts by weight of poloxamer and 0.5-2 parts by weight of hydroxypropyl methylcellulose (HPMC).

More preferably, the present invention provides a composition for use in bone implantation comprising:

A) 30-55 wt % of calcium phosphate compound particles in the form of microsphere; and B) 45-70 wt % of a biodegradable hydrogel containing, based on 100 parts by weight of the hydrogel, 25-35 parts by weight of poloxamer and 0.5-2 parts by weight of hydroxypropyl methylcellulose (HPMC).

The present invention also provides a kit for bone implantation comprising:

a bone graft composition comprising A) 30-55 wt % of calcium phosphate compound particles, and B) 45-70 wt % of a biodegradable hydrogel containing, based on 100 parts by weight of the hydrogel, 25-35 parts by weight of poloxamer and 0.5-2 parts by weight of hydroxypropyl methylcellulose (HPMC); and an injection tool.

In the present invention, the injection tool may be a syringe, a tube or the like.

MODE FOR THE INVENTION

Hereinafter, the present invention will be described in further detail with reference to examples. It is to be understood, however, that these examples are for illustrative purposes and are not intended to limit the scope of the present invention.

PREPARATION EXAMPLE 1

Preparation of β-TCP Microsphere

Pure β-TCP powder (Cerectron Co., Ltd., Korea) was spray-dried to make spherical powder. Then, the spherical β-TCP powder was sintered at a temperature of 1050° C., and the sintered particles were sieved in the range of 45-75 μm.

EXPERIMENTAL EXAMPLE 1

Selection of Poloxamer Concentration

In order to determine the optimal concentration of poloxamer in a hydrogel that is used in a bone graft material, the change in physical properties with the concentration of poloxamer was examined.

Specifically, poloxamer 407 (BASF, Pluronic F-127) and purified water were placed in a high-speed vacuum mixer and uniformly mixed each other at various concentrations to prepare poloxamer hydrogels. Then, the strength, hardness, adhesiveness and maximum stress of each of the prepared hydrogels were examined. Herein, the compressive strength, yield strength and adhesiveness of each hydrogel were measured with a rheometer (COMPAC-100, SUN SCIENTIFIC, Japan) at a temperature of 37° C.

As a result, it was shown that all the properties of the hydrogel having a poloxamer concentration of less than 20 wt % were significantly inferior to those of the hydrogel having a poloxamer concentration of 30 wt % and that all the properties of the hydrogel having a poloxamer concentration of more than 35 wt % were not significantly improved compared to those of the hydrogel having a poloxamer concentration of 30 wt %.

Figure 1:
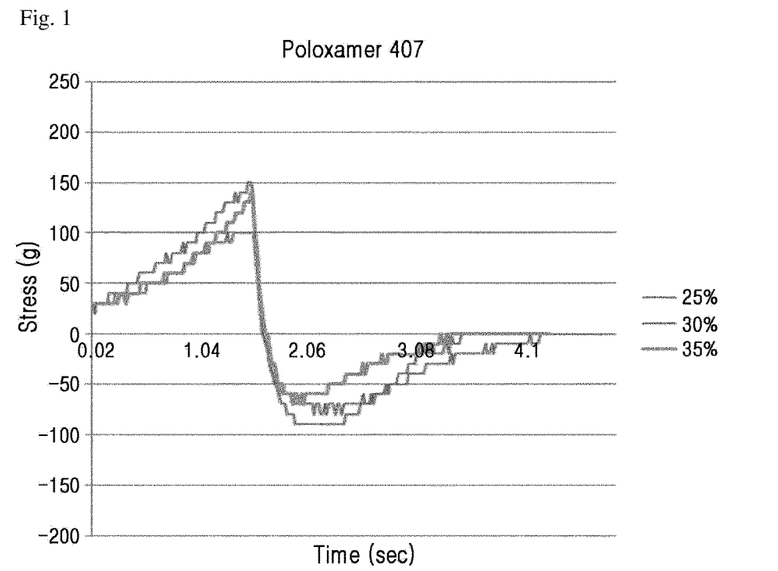
FIG. 1 shows the results of measuring the compressive strength of poloxamer 407 hydrogel at various concentrations.

Specifically, the results of examining the physical properties of each of the hydrogels having poloxamer concentrations of 25 wt %, 30 wt % and 35 wt % are shown in FIG. 1 and Table 1 below.

FIG. 1 shows the results of measuring the compressive strengths of poloxamer 407 hydrogel at various concentrations.

TABLE 1

| Concentration of poloxamer 407 | Strength (g/cm$^2$) | Adhesiveness (g) |
|---|---|---|
| 25 wt % | 140 | 83 |
| 30 wt % | 212 | 90 |
| 35 wt % | 237 | 113 |

From the results in FIG. 1 and Table 1, it can be seen that the poloxamer concentration range of 30-35 wt % is the optimal concentration.

EXPERIMENTAL EXAMPLE 2

Selection of Auxiliary Component that Improves Dispersibility and Viscoelasticity and the Content Thereof When a bone graft material is filled in bone defects, the formulation can dissolve while the hydrogel can be diluted with the surrounding blood flow. In order to minimize dispersibility caused by a blood flow, it is required to improve the dispersibility and viscoelasticity of a hydrogel that is used in the bone graft material. Particularly, when poloxamer comes into contact with water, the contact surface is quickly degraded, and for this reason, it is required to add an auxiliary component capable of improving viscoelasticity and dispersibility caused by a blood flow. In this example, chitosan, HPMC and alginate were preliminarily selected.

The preliminarily selected chitosan, HPMC and alginate were added in the same amount (0.5 wt %), and the change in viscosity caused by each of the auxiliary hydrogels added in a trace amount was measured. The measurement of viscosity was performed using a viscometer for high viscosity (Viscometer DVII+ Pro, Brookfield, USA) at a speed of 20 rpm and at a temperature of 37° C.

Figure 2:
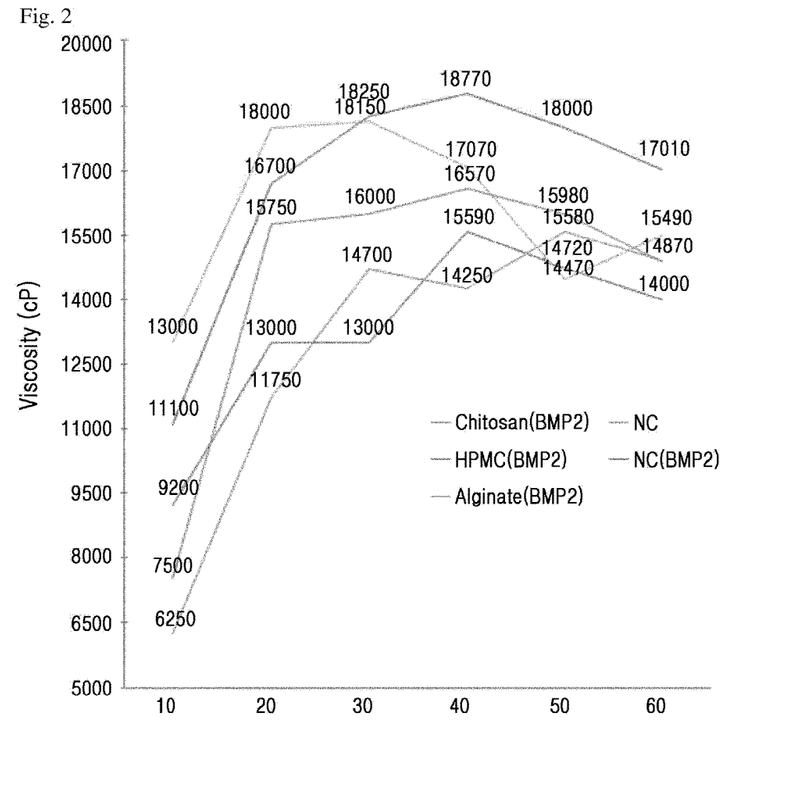
FIG. 2 shows the results of measuring a change in viscosity after adding chitosan, HPMC or alginate to poloxamer in order to select an auxiliary component capable of improving the dispersibility and viscoelasticity of a hydrogel that is used in a bone graft material.

The results of the measurement are shown in FIG. 2.

From the results in FIG. 2, it can be seen that the addition of HPMC showed significantly better viscosity properties compared to the addition of chitosan or alginate.

Accordingly, HPMC was selected as an auxiliary component for the hydrogel.

Further, in order to determine the optimal content of HPMC, HPMC was combined with poloxamer at various content ratios to prepare hydrogels, and then a compressive strength test for the prepared hydrogels was performed. When HPMC is added to prepare highly elastic hydrogels, it is impossible to measure the physical properties of the hydrogels with a rotation-type viscometer for high viscosity. For this reason, the physical properties were evaluated by the compressive strengths and analyzed using a rheometer (COMPAC-100, SUN SCIENTIFIC, Japan) at 37° C.

When HPMC was added to the hydrogel having a poloxamer concentration of 35 wt %, the agglomeration of HPMC was observed. For this reason, in the following compressive strength test, various amounts of HPMC were added to each of the hydrogel having a poloxamer concentration of 25 wt % and the hydrogel having a poloxamer concentration of 30 wt % as shown in Table 2 below.

TABLE 2

| P25H2 - 25 wt % poloxamer plus 2 wt % HPMC | P30H2 - 30 wt % poloxamer plus 2 wt % HPMC |
| P25H1 - 25 wt % poloxamer plus 1 wt % HPMC | P30H1 - 30 wt % poloxamer plus 1 wt % HPMC |
| P25H05 - 25 wt % poloxamer plus 0.5 wt % HPMC | P30H05 - 30 wt % poloxamer plus 0.5 wt % HPMC |

Figure 3A:
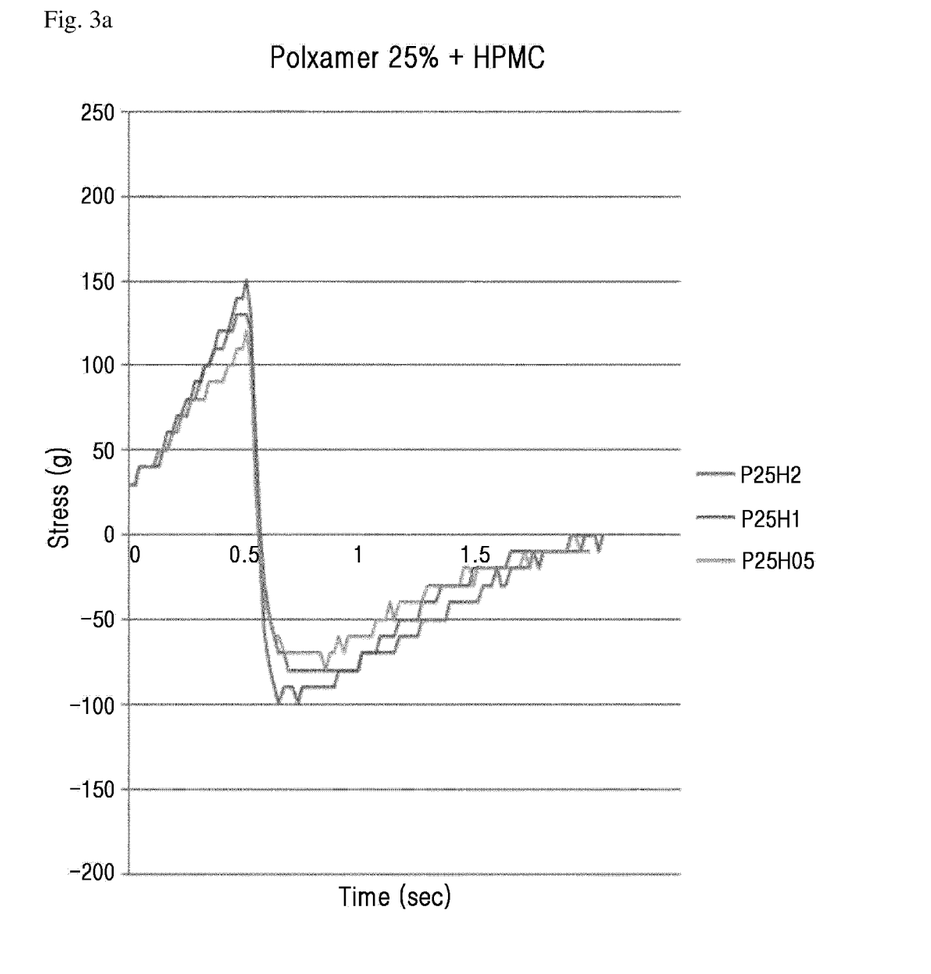
FIGS. 3a and 3b show the results of performing a compressive strength test after combining HPMC with poloxamer at various content ratios to prepare hydrogels.
Figure 3B:
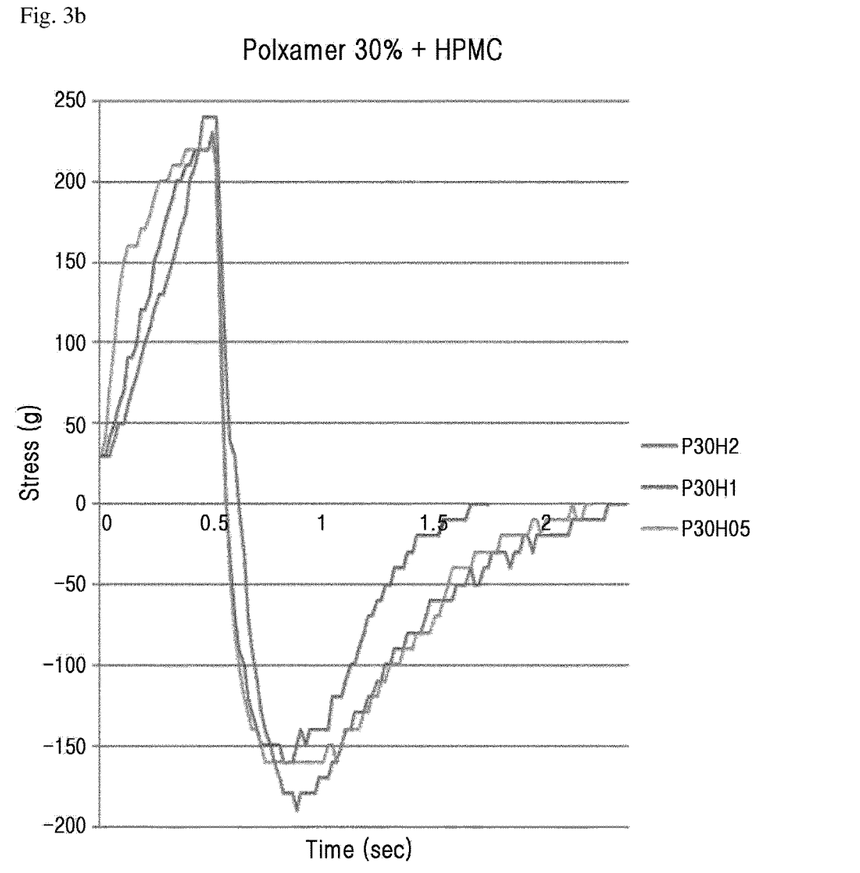

The results of the compressive strength test are shown in FIG. 3.

From the results in FIG. 3, it can be seen that, when various amounts of HPMC (0.5 wt %, 1 wt % and 2 wt %) were added to each of the 25 wt % poloxamer hydrogel and the 30 wt % poloxamer hydrogel, the compressive strength of the 30 wt % poloxamer hydrogel was about 1.5 times higher than that of the 25 wt % poloxamer hydrogel.

Accordingly, hydrogels having a fixed poloxamer content of 30 wt % and containing various amounts of HPMC were prepared, and then the physical properties thereof were examined. When the content of HPMC was more than 2 wt %, melting for a long period of time at 80° C. was required, resulting in a decrease in workability. Accordingly, in the following test, hydrogels having various HPMC contents of 0.5 wt %, 1 wt % and 2 wt % were prepared, and then the physical properties thereof were analyzed.

The results of the analysis are shown in Table 3 below.

TABLE 3

| | Strength (g/cm$^2$) | Adhesiveness (g) |
|---|---|---|
| 30 wt % poloxamer + 0.5 wt % HPM | 140 | 150 |
| 30 wt % poloxamer + 1 wt % HPMC | 220 | 160 |
| 30 wt % poloxamer + 2 wt % HPMC | 305 | 190 |

From the results in Table 3, it can be seen that the hydrogel having a HPMC content of 2 wt % showed the best physical properties. When HPMC was added in an amount of more than 2 wt %, the viscoelasticity of the hydrogel was extremely increased, making it impossible to mix poloxamer, and for this reason, the maximum content of HPMC was set at 2 wt %.

Thus, from the results of Experimental Examples 1 and 2 above, it can be seen that the hydrogel most preferably has a poloxamer content of 30 wt %, a HPMC content of 2 wt % and a water content of 70 wt %.

EXPERIMENTAL EXAMPLE 3

Determination of Content of β-TCP

A hydrogel having a poloxamer content of 30 wt %, a HPMC content of 2 wt % and a water content of 70 wt %, determined to be the optimal contents in Experimental Examples 1 and 2 above, was prepared, and then bone graft compositions were prepared by mixing the hydrogel with different amounts of the β-TCP microsphere prepared in Preparation Example 1, and the physical properties thereof were analyzed.

Figure 4A:
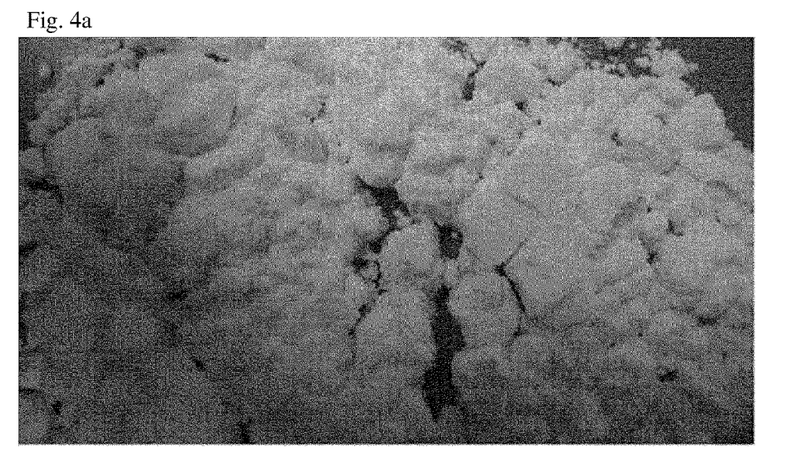
FIG. 4a shows the case in which the content of β-TCP powder is 70 wt %.
Figure 4B:
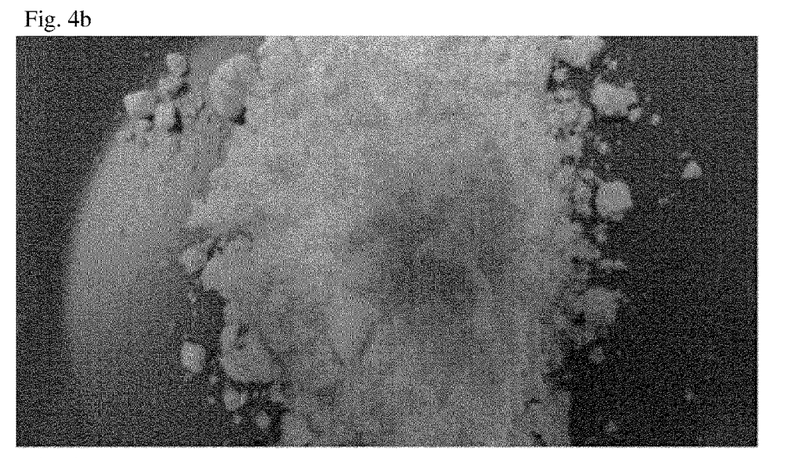
FIG. 4b shows the case in which the content of β-TCP powder is 60 wt %.
Figure 4C:
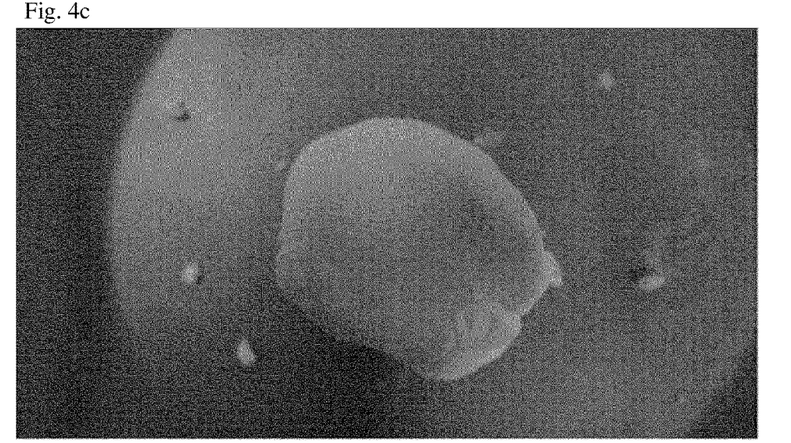
FIG. 4c shows the case in which the content of β-TCP powder is 50 wt %.
Figure 4D:
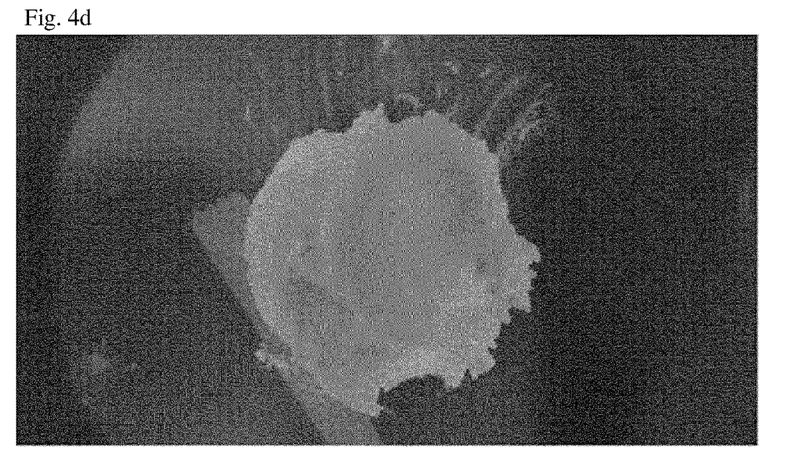
FIG. 4d shows the case in which the content of β-TCP powder is 45 wt %.
Figure 4E:
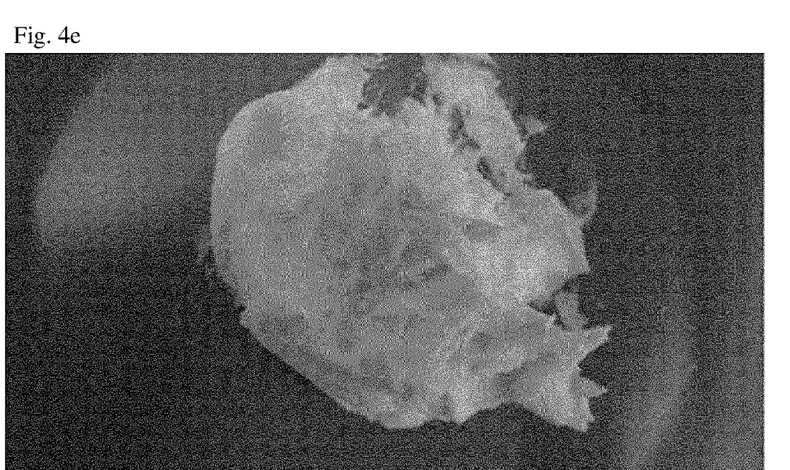
FIG. 4e shows the case in which the content of β-TCP powder is 40 wt %.
Figure 4F:
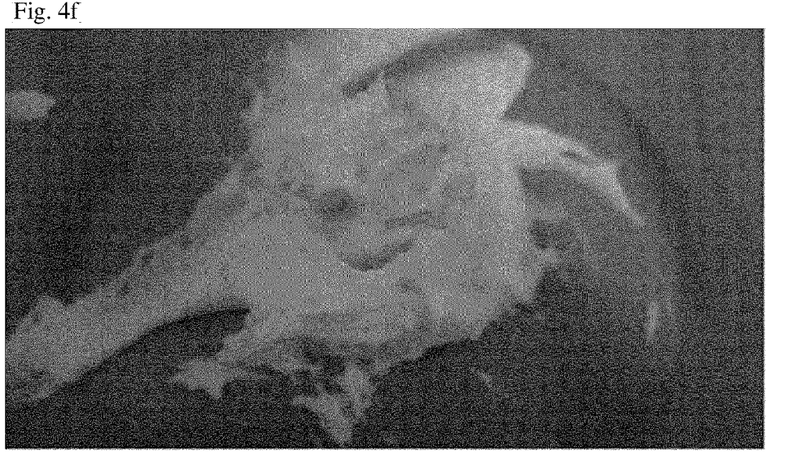
FIG. 4f shows the case in which the content of β-TCP powder is 30 wt %.

The results of the analysis are shown in FIGS. 4a to 4f. Specifically, FIG. 4a shows the case in which the content of β-TCP microsphere is 70 wt %; FIG. 4b shows the case in which the content of β-TCP microsphere is 60 wt %; FIG. 4c shows the case in which the content of β-TCP microsphere is 50 wt %; FIG. 4d shows the case in which the content of β-TCP microsphere is 45 wt %; FIG. 4e shows the case in which the content of β-TCP microsphere is 40 wt %; and FIG. 4f shows the case in which the content of β-TCP microsphere is 30 wt %.

From FIGS. 4a to 4b, it can be seen that the hydrogels are in the form of powder due to the insufficient content of gel and cannot be injected. On the other hand, from FIGS. 4c to 4f, it can be seen that the hydrogels are in an injectable putty form due to the sufficient content of gel.

Particularly, in the case of FIG. 4c showing the bone graft composition having a β-TCP microsphere content of 50 wt %, that is, a content ratio of gel to microsphere of 1:1, it can be seen that the putty-type bone graft composition does not stick to hand due to its low adhesiveness, suggesting that it has good workability. In addition, in the case in which the content ratio of gel to microsphere is 1:1, the maximum stress of the bone graft composition is high, and thus the composition has high resistance to an external force that is applied thereto. Thus, in this case, the loss of the material during closure can be prevented, and the material can be prevented from being dissolved due to the bleeding of an incised surface in a surgical site. In addition, because the bone graft material has low adhesiveness, it cannot stick not only to hand, but also to a device, during surgery.

Therefore, the above results suggest that the optimal content of β-TCP microsphere is 50 wt % and that β-TCP microsphere can be used in an amount ranging from 30 to 55 wt % in view of injectability.

EXAMPLE 1

Preparation of Bone Graft Composition of the Present Invention

Based on the results of Experimental Examples 1 to 3, a bone graft composition was prepared in the following manner.

First, 1 g of HPMC and 10 ml of purified water were placed in a high-speed vacuum mixer and uniformly mixed with each other at a speed of 400 rpm. Then, 10 ml of purified water was added to the semi-transparent jelly-type HPMC gel and mixed at the same speed, after which 14 ml of purified water was further added, and the HPMC gel was uniformly mixed. Then, 15 g of poloxamer 407 was added to the HPMC gel, followed by mixing at a speed of 400 rpm (hydrogel comprising 30 wt % of poloxamer and 2 wt % of HPMC). 50 g of β-TCP microspheres were added to the resulting gel and uniformly mixed at a low speed of 200 rpm or lower, thereby obtaining a bone graft composition.

COMPARATIVE EXAMPLE 1

Preparation of Bone Graft Composition Having BMP-2 and Containing No HPMC

First, 35 g of poloxamer 407 and 65 g of purified water were mixed with each other at 4° C. and completely dissolved to prepare a gel containing 35 wt % of poloxamer 407. The gel containing 35 wt % of poloxamer 407 was placed in a Luer-Lock type syringe.

0.35 ml (70 wt % based on β-TCP) of BMP-2 solution was absorbed into a syringe, containing 0.5 g of the β-TCP microspheres prepared in Preparation Example 1, by the use of a syringe needle.

The syringe containing the poloxamer 407 gel and the syringe containing the β-TCP microspheres having BMP-2 absorbed therein were connected to a 3-way connector, and then the contents of the two connected syringes were uniformly mixed using the connector, thereby obtaining a bone graft composition.

COMPARATIVE EXAMPLE 2

Preparation of Bone Graft Composition Containing No HPMC

A bone graft composition was prepared in the same manner as described in Comparative Example 1, except that the BMP-2 solution was not used. In other words, the bone graft composition was prepared without performing the process of absorbing the BMP-2 solution into the β-TCP microspheres.

EXPERIMENTAL EXAMPLE 4

Figure 5:
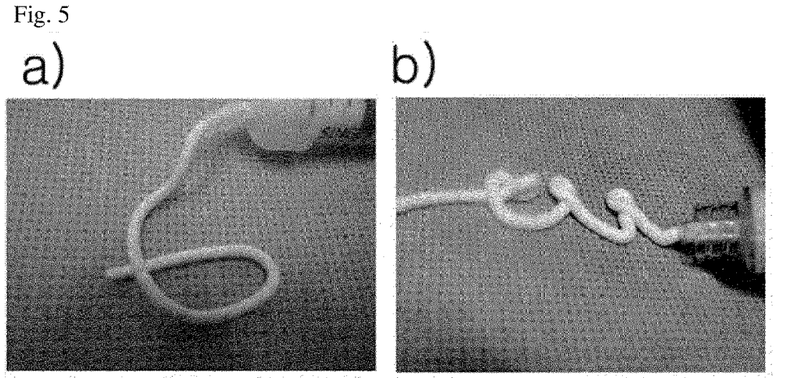
FIG. 5 is a set of photographic views showing the appearances of bone graft compositions of Example 1 and Comparative Example 1.

Examination of External Shape of Bone Graft Composition of the Present Invention and Water Resistance of the Bone Graft Composition FIG. 5 shows the appearances of the bone graft compositions of Example 1 and Comparative Example 1.

Specifically, FIG. 5*a* shows the appearance of the bone graft composition of Example 1, and FIG. 5*b* shows the appearance of the bone graft composition of Comparative Example 1.

As can be seen from the appearances in FIGS. 5*a* and 5*b*, the bone graft composition of the present invention has a highly elastic and hard shape.

In addition, the water resistances of the bone graft compositions of Example 1 and Comparative Example 1 were examined.

Specifically, the bone graft compositions of Example 1 and Comparative Example 1 were immersed in water at 37° C., and whether the external shapes thereof were maintained with the passage of time was observed.

Figure 6:
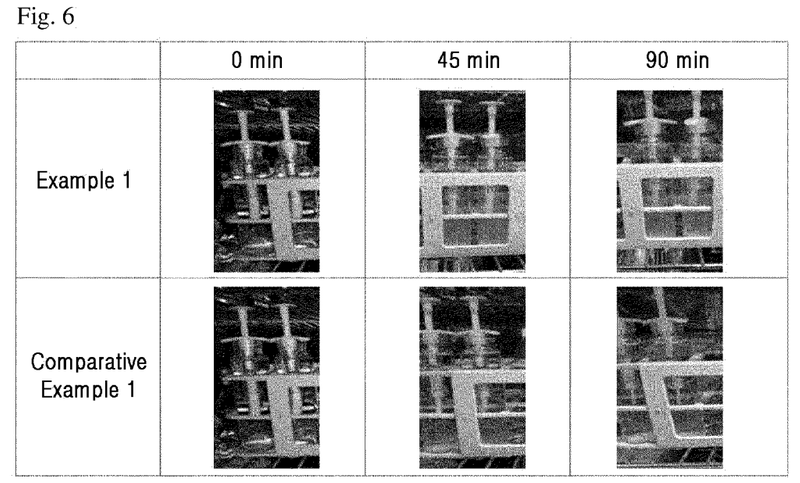
FIGS. 6 and 7 show the results of examining the water resistances of bone graft compositions of Example 1 and Comparative Example 1.
Figure 7:
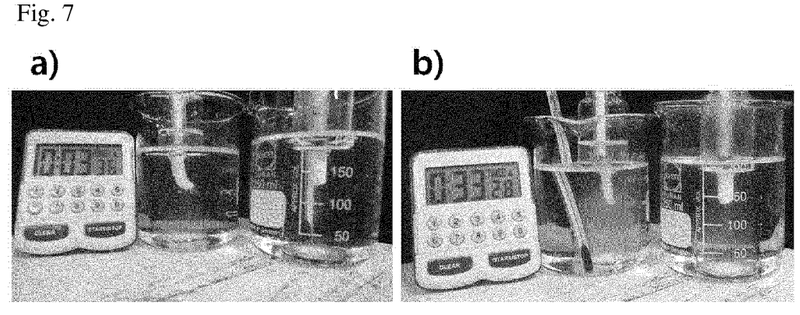

The results of the observation are shown in FIGS. 6 and 7. FIG. 7*a* shows the results for the bone graft composition of Comparative Example 1, and FIG. 7*b* shows the results for the bone graft composition of Example 1. As can be seen in FIGS. 6 and 7, the bone graft composition of the present invention has high resistance to water, and thus the external shape thereof can be maintained for a period of time that is at least two times longer than that of the bone graft composition of Comparative Example 1. Particularly, the bone graft composition of Comparative Example 1 in water at 37° C. lost the ability to fix the formulation from 3 minutes, and the diffusion thereof in water became severe after 30 minutes, suggesting that the loss of the bone graft composition occurred, whereas the bone graft composition of Example 1 stably maintained its shape for 30 minutes, suggesting that it has low dispersibility in blood.

EXPERIMENTAL EXAMPLE 5

Examination of Physical Properties of Bone Graft Composition of the Present Invention The physical properties of the bone graft compositions of Example 1 and Comparative Examples 1 and 2 were examined.

The results of the examination are shown in Table 4 below and FIGS. 8 and 9.

TABLE 4

|  | Compressive strength (g/cm$^2$) | Yield strength (g/cm$^2$) | Adhesiveness (g) |
|---|---|---|---|
| Comparative Example 1 | 153 | 110 | −70 |
| Comparative Example 2 | 142 | 93.36 | −50 |
| Example 1 | 3340 | 2253.33 | −10 |

Figure 8:
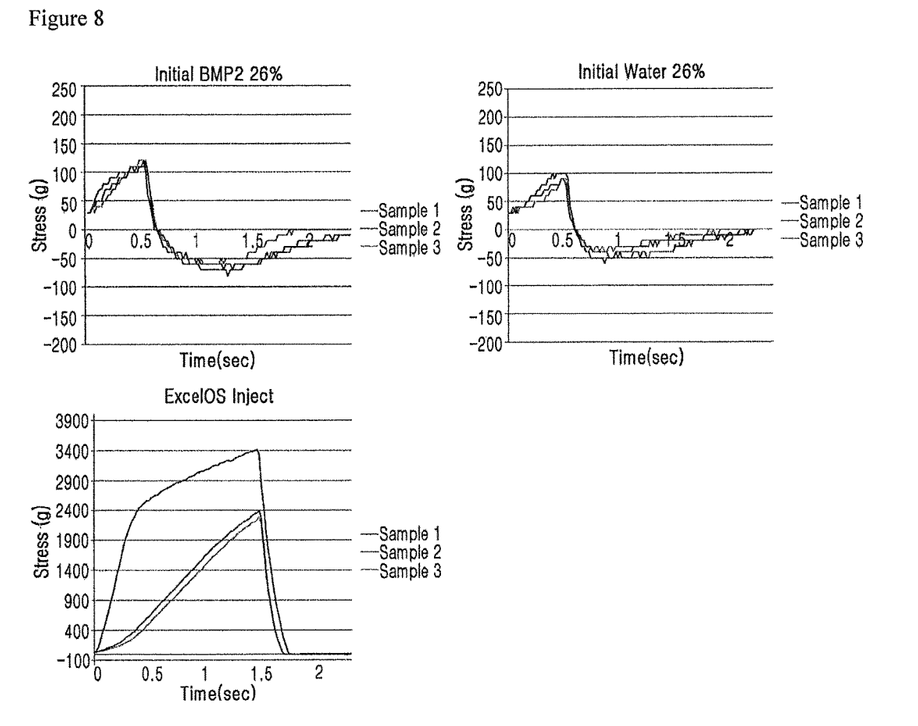
FIGS. 8 and 9 shows the results of examining the physical properties of bone graft compositions of Example 1 and Comparative Example 1.
Figure 9:
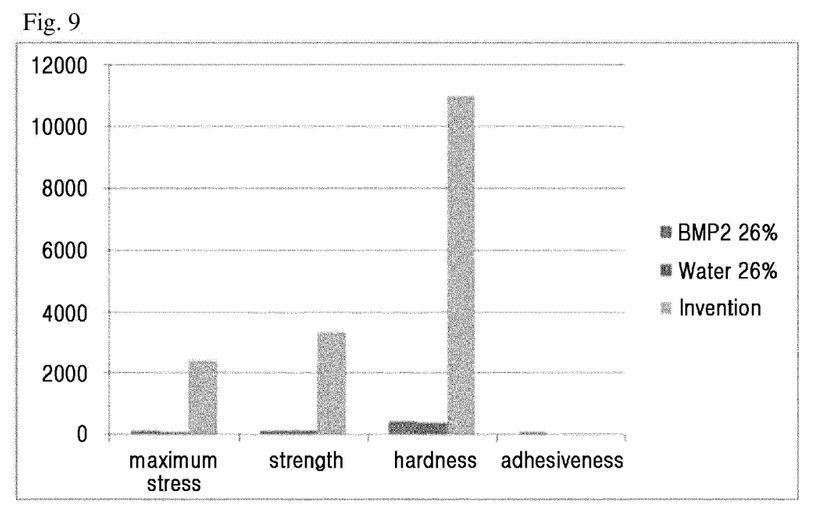

As can be seen in Table 4 and FIGS. 8 and 9, the bone graft composition of Example 1 has better physical properties than the bone graft compositions of Comparative Examples 1 and 2. Particularly, it could be seen that the bone graft composition of Example 1 had high strength, and thus had high resistance to an external force applied thereto, suggesting that the loss of the material during closure can be prevented and that the material can be prevented from being dissolved due to the bleeding of an incised surface in a surgical site. In addition, it can be seen that the bone graft composition of Example 1 showed high yield strength due to its high elastic property, whereas the bone graft composition of Comparative Example 1 had no elasticity, and thus showed a yield strength value almost equal to the compressive strength.

Figure 10:
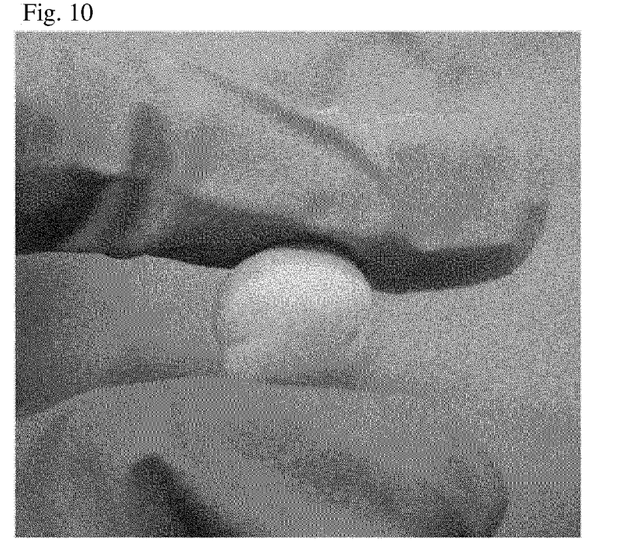
FIG. 10 is a photographic view showing that a bone graft composition of Example 1 does not stick to surgical gloves during a surgical operation performed using the bone graft composition.

Furthermore, it could be seen that the bone graft composition of Example 1 had low adhesiveness, and thus did not stick to surgical gloves as shown in FIG. 10.

EXPERIMENTAL EXAMPLE 6

Animal Test For Bone Graft Composition of the Present Invention

Each of the bone graft compositions of Example 1 and Comparative Examples was implanted into animal bone defects, and then the level at which the formulation was maintained by cramming was evaluated.

Figure 11:
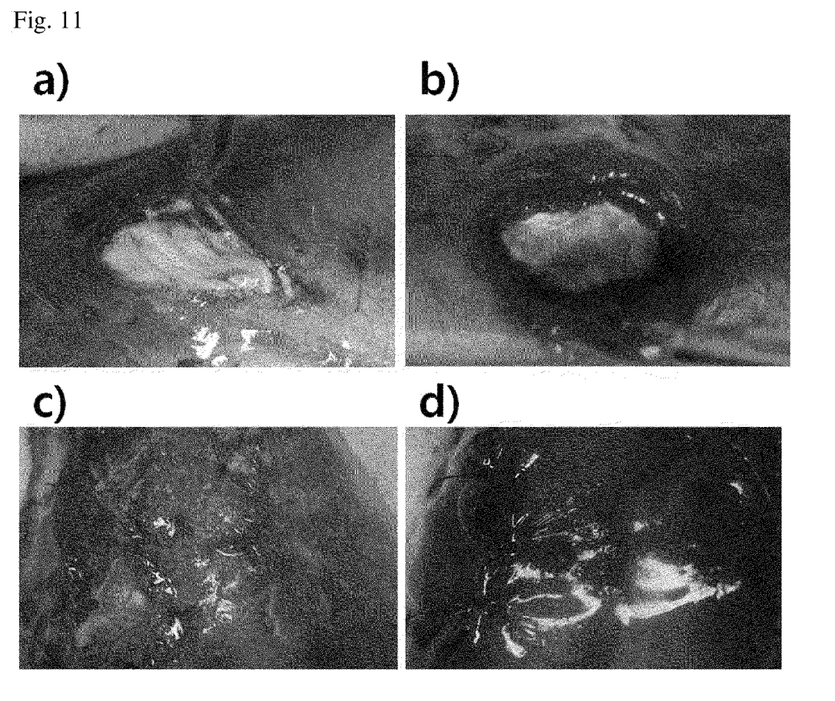
FIG. 11 shows the results of observing the level at which the formulation of each of bone graft compositions of Example 1 and Comparative Example 1 is maintained by cramming after implantation into animal bone defects.

The results of the evaluation are shown in FIG. 11. Specifically, FIG. 11a shows the bone graft composition of Comparative Example 1 immediately after injection; FIG. 11b shows the bone graft composition of Example 1 immediately after injection; FIG. 11c shows the bone graft composition of Comparative Example 1, crammed after injection; and FIG. 11d shows the bone graft composition of Example 1, crammed after injection.

As can be seen in FIG. 11, the bone graft composition of Comparative Example 1 started to be wet immediately after injection and was scattered around the surrounding area after cramming, whereas the bone graft composition of Example 1 showed resistance to wetting immediately after injection and did not flow to the surrounding tissue after cramming.

The invention claimed is:

1. A bone graft composition comprising:
   A) 30-55 wt % of calcium phosphate compound particles; and
   B) 45-70 wt % of a biodegradable hydrogel containing, based on 100 parts by weight of the hydrogel, 25-35 parts by weight of poloxamer and 0.5-2 parts by weight of hydroxypropyl methylcellulose (HPMC).

2. The bone graft composition of claim 1, wherein the composition has a yield strength of 1500-4000 g/cm$^2$.

3. The bone graft composition of claim 1, wherein the poloxamer has a sol-gel transition temperature of 4~35° C.

4. The bone graft composition of claim 1, wherein the composition comprises the hydrogel filled between the calcium phosphate compound particles close to each other.

5. The bone graft composition of claim 1, wherein the calcium phosphate compound is tricalcium phosphate (TCP), monocalcium phosphate, tetracalcium phosphate, dicalcium phosphate, hydroxyapatite, or a combination of two or more thereof.

6. The bone graft composition of claim 5, wherein the tricalcium phosphate is β-tricalcium phosphate (β-TCP).

7. The bone graft composition of claim 6, wherein the β-TCP is in the form of microspheres.

8. The bone graft composition of claim 7, wherein the β-TCP is obtained by spray-drying β-TCP powder, sintering the dried powder at a temperature of 1050~1250° C. and sieving the sintered powder in the range of 45-75 μm.

9. The bone graft composition of claim 1, wherein the poloxamer is poloxamer 407.

10. The bone graft composition of claim 1, wherein the HPMC has a viscosity of 1,000-100,000 cps.

11. The bone graft composition of claim 1, further comprising bone morphogenetic protein (BMP).

12. The bone graft composition of claim 11, wherein the bone morphogenetic protein is BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, or a combination of two or more thereof.

13. A method for preparing a bone graft composition of claim 1, the method comprising the steps of:
   1) preparing a biodegradable hydrogel containing, based on 100 parts by weight of the hydrogel, 25-35 parts by weight of poloxamer and 0.5-2 parts by weight of hydroxypropyl methylcellulose (HPMC); and
   2) mixing 30-55 wt % of calcium phosphate compound particles with 45-70 wt % of the biodegradable hydrogel.

14. The method of claim 13, wherein bone morphogenetic protein (BMP) is further added and mixed in step 2).

15. The method of claim 14, wherein the bone morphogenetic protein is BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, or a combination of two or more thereof.

16. A kit for bone implantation comprising: the bone graft composition according to claim 1; and an injection tool.

17. The kit of claim 16, wherein the injection tool is a syringe or a tube.

18. A kit for bone implantation comprising: the bone graft composition according to claim 2; and an injection tool.

19. A kit for bone implantation comprising: the bone graft composition according to claim 3; and an injection tool.

20. A kit for bone implantation comprising: the bone graft composition according to claim 4; and an injection tool.

* * * * *